United States Patent
Jerebko (10) Patent No.: US 8,503,755 B2
(45) Date of Patent: Aug. 6, 2013

(54) TOMOSYNTHESIS METHOD WITH AN ITERATIVE MAXIMUM A POSTERIORI RECONSTRUCTION

(75) Inventor: Anna Jerebko, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 318 days.

(21) Appl. No.: 13/051,569

(22) Filed: Mar. 18, 2011

(65) Prior Publication Data

US 2011/0229007 A1    Sep. 22, 2011

(30) Foreign Application Priority Data

Mar. 18, 2010  (DE) .......................... 10 2010 011 911

(51) Int. Cl.
*G06K 9/00* (2006.01)

(52) U.S. Cl.
USPC ......................................................... 382/132

(58) Field of Classification Search
USPC ................ 382/131, 132; 378/5, 8, 21, 62, 63, 378/90, 91, 165; 348/77
See application file for complete search history.

(56) References Cited

U.S. PATENT DOCUMENTS

| | | | | |
|---|---|---|---|---|
| 5,376,795 | A * | 12/1994 | Hasegawa et al. ....... | 250/363.04 |
| 7,945,014 | B2 | 5/2011 | Mertelmeier | |
| 2006/0104406 | A1 * | 5/2006 | Siltanen et al. ................... | 378/4 |
| 2007/0217666 | A1 * | 9/2007 | Gal et al. ...................... | 382/131 |
| 2008/0013672 | A1 * | 1/2008 | Krauss et al. ..................... | 378/4 |
| 2009/0310844 | A1 | 12/2009 | Ludwig et al. | |
| 2010/0034450 | A1 | 2/2010 | Mertelmeier | |
| 2010/0207629 | A1 * | 8/2010 | Trzasko et al. ................ | 324/309 |
| 2011/0013817 | A1 * | 1/2011 | Medow .......................... | 382/131 |

OTHER PUBLICATIONS

Jerebko et al ("Regularization Parameter Selection in Maximum a Posteriori Iterative Reconstruction for Digital Breast Tomosynthesis", Digital Mammography, Lecture Notes in Computer Science vol. 6136, 2010, pp. 548-555, Jun. 16-18, 2010).*
"An Anatomically Based Regionally Adaptive Prior for MAP Reconstruction in Emission Tomography," Chan et al., 2007 IEEE Nuclear Science Symposium Conference Record, pp. 4137-4140.
"Dose reduction in breast tomosynthesis using a penalized maximum likelihood reconstruction," Das et al., Proc. of SPIE, vol. 7258 (2009), pp. 725855-1-725855-8.
Globally Convergent Algorithms for Maximum *a Posteriori* Transmission Tomography, Lange et al., IEEE Trans. on Image Processing, vol. 4, No. 10 (1995), pp. 1430-1438.
"Regularization Parameter Selection in Maximum a Posteriori Iterative Reconstruction for Digital Breast Tomosynthesis," Jerebko et al., Siemens AG (2010).
"Simulation Evaluation of Gibbs Prior Distributions for Use in Maximum *A Posteriori* SPECT Reconstructions," Lalush et al., IEEE Trans. on Medical Imaging, vol. 11, No. 2 (1992), pp. 267-275.
"An Efficient Maximum-Likelihood Reconstruction Algorithm for Transmission Tomography and a Generalized Geman Prior," De Man et al., Presentation at RSNA 2005.

* cited by examiner

*Primary Examiner* — Jason M Repko
*Assistant Examiner* — Shervin Nakhjavan
(74) *Attorney, Agent, or Firm* — Schiff Hardin LLP (57) ABSTRACT

In a maximum a posteriori tomosynthesis method to reconstruct a three-dimensional image from two-dimensional x-ray images, a Geman prior function to reduce the noise is used in which the edges and boundaries of tissue structures remain visible. The method is parameterized by the estimated noise value of the attenuation coefficients and the estimated average tissue attenuation value.

14 Claims, 5 Drawing Sheets

TOMOSYNTHESIS METHOD WITH AN ITERATIVE MAXIMUM A POSTERIORI RECONSTRUCTION

BACKGROUND OF THE INVENTION

1. Field of the Invention

The present invention concerns an iterative tomosynthesis method that uses an iterative maximum a posteriori reconstruction, and in particular the analytical determination of the parameters of a prior function used in maximum a posteriori iterative reconstruction.

2. Description of the Prior Art

In tomosynthesis, a three-dimensional image is generated from a number of two-dimensional images. By means of an x-ray device with an x-ray source and a detector, a two-dimensional image or a projection of the tissue to be examined is generated from each position of x-ray source trajectory. Each two-dimensional image depicts the attenuation of the tissue in the volume that the beam has propagated through. A second two-dimensional image or a second projection of the same tissue is acquired after the beam source and/or the detector have been moved into a second position. After a number of such two-dimensional images have been acquired, a three-dimensional tomosynthesis image can be generated by means of a reconstruction. The present invention can be used in three-dimensional tomosynthesis in an x-ray technique, computed tomography, or in magnetic resonance tomography.

One field of application of the aforementioned three-dimensional imaging method is mammography. An image generation device typically used in mammography has a pivotable x-ray source and a stationary x-ray detector. The tissue to be examined is positioned over the stationary detector. The x-ray source is subsequently panned in multiple steps, for example in a range of +/−25°, and a number of two-dimensional x-ray images respectively from different pan positions of the x-ray source are acquired with the stationary detector. Naturally, it is also possible to use a number of stationary x-ray sources or to only shift the x-ray source in translation. The detector also be shifted or panned counter to the movement of the x-ray source. A three-dimensional image is generated by means of reconstruction from the plurality of two-dimensional x-ray images. Known imaging methods and devices for mammography are described in DE 10 2006 046 741 A1, DE 10 2008 004 473 A1 and DE 10 2008 028 387 A1, for example.

In the prior art a technique known as filtered back-projection is used to reconstruct a three-dimensional image from a number of two-dimensional images. Filtered back-projection is described in Imaging Systems for Medical Diagnostics, Arnulf Oppelt, Publicis Corporate Publishing, Erlangen, ISBN 3-89578-226-2, Chapter 10.5. These filtered back-projection reconstruction methods depict reconstructed images with a high contrast and a high degree of accuracy of detail but, in tomosynthesis with a limited scan angle, lose information about the relative tissue density due to the missing data. This happens in part because specific filter kernels remove low-frequency portions. In general, digital breast tomosynthesis (DBT) is negatively affected by incomplete data and a poor quantum statistic that is limited by the total dose that is absorbed in the breast. The breast is composed primarily of glandular tissue, adipose tissue, connective tissue and blood vessels. The coefficients of x-ray attenuation of these tissue type are very similar, which significantly hinders the evaluation of three-dimensional mammography images. The primary field of application of imaging methods in mammography is the early detection of cancerous tissue. This is made even more difficult because cancerous tissue has a coefficient of x-ray attenuation that is similar to that of other tissue types. Mammography methods are described in Imaging Systems for Medical Diagnostics, Arnulf Oppelt, Chapter 12.6, Publicis Corporate Publishing, Erlangen, ISBN 3-89578-226-2.

An additional problem of the aforementioned filtered back-projection reconstruction methods is that artifacts outside of the plane where the object is in focus (known as out-of-plane artifacts) are intensified by the filtering together with the image features. Statistical, iterative reconstruction methods have been suggested that maximize the similarities between the calculated and measured projections and enable a noise suppression, for example by prior functions.

Techniques known as maximum likelihood methods are employed, with which the estimated value $\mu$ of the attenuation coefficients (for example the breast volume attenuation coefficients) can be determined that maximizes the logarithmic probability function $L(\mu)$:

$$\mu_{max} = \mathrm{argmax}\{L(\mu)\};$$

The maximum likelihood reconstruction leads to comparably good results in DBT and converges in 4 to 5 iterations. One disadvantage of such reconstructions is that excessively noisy images arise without the use of prior functions or penalty functions. The use of smoothing prior functions has been proposed. The logarithmic probability function $L(\mu)$ is hereby changed into a log posterior function:

$$\Phi(\mu) = L(\mu) - \beta U(\mu);$$

wherein $U(\mu)$ is a smoothing prior function that reduces or, respectively, penalizes the differences of the values of adjacent pixels. The parameter $\beta > 0$ is a control parameter.

However, one disadvantage of this method is that the optimal parameters of the prior functions must be empirically determined, which typically comprises a search across a large value range which is undesirable given high-resolution images, in particular if multiple prior functions must be assessed.

SUMMARY OF THE INVENTION

On object of the invention is to provide an improved tomosynthesis reconstruction method that results in a three-dimensional image with a reduced noise without negatively affecting the contrast of the edges of the tissue.

According to the invention, the object is achieved by a method to determine an estimated value of an attenuation coefficient $\mu_j$ of a voxel j that is associated with a segment of a tissue. The attenuation coefficient $\mu$ indicates the attenuation per length of a radiation into the tissue, wherein the radiation is emitted by an emitter and is detected by a detector. The attenuation coefficient represents the tissue density. The estimated noise value $\Delta\tilde{\mu}$ of the voxel attenuation coefficients $\mu$ is obtained. The estimated noise value $\Delta\tilde{\mu}$ is estimated from the tissue thickness and density and information about the emitted radiation. The estimated noise value $\Delta\tilde{\mu}$ must be less than the smallest gradient to be preserved (or reconstructed). The estimated noise value $\Delta\tilde{\mu}$ is the maximum noise value that is expected in an image if no smoothing was implemented.

The estimated noise value $\Delta\tilde{\mu}$ can be determined for a given x-ray spectrum, for example as a function of the tissue thickness (for example the breast thickness) and the tube charge (mAs) using regression methods. In general, the noise level can be kept constant for an arbitrary breast thickness via the selection of the tube charge and the photon energy (keV).

The average tissue attenuation coefficient $\bar{\mu}$ is estimated. The average tissue attenuation coefficient $\bar{\mu}$ is estimated on the basis of the energy of the radiation emitted from the emitter and on the basis of a tissue density estimate. For example, the estimated average tissue attenuation value can $\bar{\mu}$ be estimated on the basis of the photon energy and a breast thickness estimation that are determined via segmented original projections using conventional methods.

The estimated noise value $\Delta\tilde{\mu}$ and the average tissue attenuation coefficient $\bar{\mu}$ and its dependency on the aforementioned physical variables can be determined by means of statistical methods on a plurality of patient images or tissue samples. The estimated noise value $\Delta\tilde{\mu}$ and the average tissue attenuation coefficient $\bar{\mu}$ can be determined via a statistical study of several ($n \geq 5$) patient images or tissue samples or a larger number of patients or, respectively, tissue samples. The connection between the estimated noise value $\Delta\tilde{\mu}$ and the average tissue attenuation coefficient $\bar{\mu}$ and the aforementioned physical variables can be determined via a regression method. The estimated noise value $\Delta\tilde{\mu}$ is the highest noise value to be compensated.

The parameters of a prior function $U(\mu)$ are calculated from the expected noise value $\Delta\tilde{\mu}$ and the estimated average tissue attenuation value $\bar{\mu}$. The estimated value of the attenuation coefficients $\mu_j$ of a voxel is subsequently calculated iteratively from projection data acquired by means of the detector, the estimated noise value $\Delta\tilde{\mu}$, the average tissue attenuation coefficient $\bar{\mu}$ and the prior function $U(\mu)$. The expected noise value $\Delta\tilde{\mu}$ is that noise value that is expected in an image when no smoothing takes place by means of the prior function.

The term "voxel" designates a volume unit in three-dimensional image. It is assembled from the terms "pixel" and "volume". The prior function ensures that edges are maintained while the noise is suppressed. The attenuation can be caused due to an absorption. The attenuation coefficient can be an absorption coefficient. The attenuation can also be a (MR) spin relaxation.

The prior function $U(\mu)$ can be a Geman prior function. The Geman prior function can be determined by means of the following equation:

$$U(\mu) = \sum_j \sum_k \frac{\Delta\mu_{jk}^2 \sigma^m}{2(\sqrt{\Delta\mu_{jk}^2/2 + \sigma^2/2})^m};$$

wherein $\sigma$ is an optimization parameter and m is a constant, and wherein $\mu_j$ and $\mu_k$ are attenuation coefficients of adjacent voxels that are associated with a respective tissue segment, and j and k are linear voxel indices over three dimensions. The values of the attenuation coefficients $\mu_k$ and $\mu_j$ are updated with each iteration. This means that in the first iteration these values are pre-populated with estimated values, for example with the average estimated tissue value. In the subsequent iterations those values that have been determined in the preceding iteration are used for the attenuation coefficients $\mu_k$ and $\mu_j$. For example, a neighborhood of 3×3×3 voxels can be evaluated in order to determine the differences $\mu_k$ of the tissue attenuation coefficients.

The prior function for the respective application field can be optimized by means of the parameters β, σ and m. β, σ and m are selected in order to retain the edges of the image as well as possible and m is selected so that the prior function assumes a convex form to ensure the convergence.

Before the image was reconstructed, the differences $\Delta\mu_{jk}$ are not known. If the reconstruction method is applied to data that were generated by means of x-rays, it is assumed that the noise in the projection i is spatially independent. Therefore, to determine the optimal value for the parameter σ in the Geman prior function the term $\Delta\mu_{jk}$ is replaced by the estimated noise value, the maximum estimated noise value $\Delta\tilde{\mu}$. If the image data were acquired by means of a magnetic resonance scanner, the noise can be spatially dependent. In this case the value $\Delta\tilde{\mu}_j$ can be dependent on the location of the voxel j.

However, it is also possible to determine the values $\mu_j$ and $\mu_k$ and thus $\Delta\mu_{jk}$ by means of conventional reconstruction methods, for example by means of a linear and/or filtered back production. The parameter σ thus can be determined more precisely.

In the event that the prior function should have a convex shape, σ is selected so that the first derivative of the prior function reaches its highest point of curvature at values of $\Delta\mu$ that correspond to the estimated noise value $\Delta\tilde{\mu}$. m is should be $\leq 16/17$.

In the event that the prior function has a non-convex shape, σ is selected so that the first derivative of the prior function reaches its maximum at values of $\Delta\mu$ that correspond to the estimated noise value $\Delta\tilde{\mu}$. m is =2.

The method also has the step of the iterative calculation of the estimated value of the attenuation coefficient $\mu_j$ of a voxel j to reconstruct a three-dimensional image by means of the following formula:

$$\mu_j^{n+1} = \mu_j^n + \frac{\mu_j^n}{\sum_i Y_i l_{ij} + \beta \mu_j^n \frac{\partial^2}{\partial \mu_j^2} U(\mu^n)} \frac{\partial}{\partial \mu_j} \Phi(\mu^n);$$

wherein β is an optimization parameter and $\phi(\mu^n) = L(\mu) - \beta U(\mu)$ is a log posterior function, $L(\mu)$ is a target function, $Y_i$ is the measured photon count of the projection i and $l_{ij}$ is the section length of the beam i through the voxel j.

This method is designated as a maximum A posteriori method with a Newton-based updating method that uses a simple quadratic smoothing prior function. The parameters δ and β can be constant in all iteration sections.

The target function $L(\mu)$ is determined as follows:

$$L(\mu) = \sum_i \{-d_i e^{-\langle l_i, \mu \rangle} - Y_i \langle l_i, \mu \rangle\} + c$$

wherein $\langle l_i, \mu \rangle = \sum_j l_{ij} \mu_j,$ i is a projection index, j is the voxel index, $d_i$ is the expected photon count that exits from the radiation source along the projection i, $Y_i$ is the detected photon count in the projection i and c is a (negligible) constant.

The control parameter β of the Geman prior function is determined before the first iteration by means of the following formula:

$$\beta = \frac{\Delta\tilde{\mu} \cdot \overline{\sum_i Y_i l_{ij}}}{\overline{\mu} \cdot \frac{\partial}{\partial \mu_j} U(\mu)\bigg|_{\Delta\mu_j = \Delta\tilde{\mu}} - \Delta\tilde{\mu} \cdot \overline{\mu} \cdot \frac{\partial^2}{\partial \mu_j^2} U(\mu)\bigg|_{\Delta\mu_j = \Delta\tilde{\mu}}};$$

wherein $\overline{\sum_i Y_i l_{ij}}$ is the average value over all voxels of the volume element across all i and j. This average value can be calculated to accelerate the iteration method once before the iterations.

However, at this point in time the difference of adjacent attenuation coefficients $\Delta\mu_{jk}$ is not yet known. If the measurement data are determined by means of x-ray radiation, it can be assumed that the noise in a projection is constant. In this case the expression $\Delta\mu_{jk}$ is therefore replaced by the maximum estimated noise value $\Delta\tilde{\mu}$. If the measurement data were generated by means of a magnetic resonance tomograph, the noise can be spatially variable, whereby the expression $\Delta\mu_{jk}$ in the Geman prior function $U(\mu)$ can be replaced with a spatially dependent estimated noise value $\Delta\tilde{\mu}_j$. As noted, the difference of the attenuation coefficients $\Delta\mu_{jk}$ can be determined before the iterations via a conventional back projection method. In this case $\beta$ can be determined more precisely.

By the determination of the parameters $\beta$ and $\sigma$, the noise level can be monitored effectively while the edges and boundaries of the tissue region are maintained. Moreover, with the present method the signal-to-noise ratio (SNR) and the contrast/noise ratio (CNR) are significantly improved. The improved signal-to-noise ratio and the improved contrast/noise ratio can have the effect that a lower radiation dose is required although three-dimensional images of better quality are achieved, which on the one hand improves the safety of the imaging procedure and on the other hand reduces the side effects of the procedure. The reduction of the value, or the penalty for voxel intensity deviations less than or equal to the highest estimated noise value, is proportional to these deviations. At the same time the edges with voxel intensity deviations that are greater than the highest estimated noise value $\Delta\tilde{\mu}$ receive only a small correction value or, respectively, penalty that corresponds to that or those of the highest estimated noise value. Given non-convex optimization method it is possible to select a Geman prior function with m=2 in which the penalty or the correction value for edge voxels is nearly zero.

The initial value $\mu_j^0$ can be established with the same value for all j. All voxels in the volume to be examined could be initialized with the average attenuation value $\mu$ of the tissue to be examined. A faster convergence can be achieved if the start value $\mu_j^0$ is pre-populated with values from normalized back-projection volume, for example as is described in the publication by Ludwig J., Mertelmeier T., Kunze H., Härer W., A Novel Approach for Filtered Projection in Tomosynthesis Based on Filter Kernels Determined by Iterative Reconstruction Techniques, Krupinski E., Lecture Notes in Computer Science 5116, Digital Mammography, 9th International Workshop, IWDM 2008, pp. 612-620, Springer Verlag Berlin Heidelberg (2008). On average 5-6 iterations are required. However, up to 20 iterations can be required. The iterative determination method can be interrupted if stopping criteria is satisfied. One possible stopping criterion is that the difference of $\mu_j^{n+1}$ and $\mu_j^n$ is less than a predetermined threshold.

The reconstruction method can be implemented by means of an iterative gradient optimization update formula. For this the step of the iterative calculation of the estimated value of the attenuation coefficient $\mu_j$ of a voxel j can be implemented by means of the following formula:

$$\mu_j^{n+1} = \mu_j^n + \mu_j^n \frac{\sum_i l_{ij}[d_i e^{-\langle l_i, \mu \rangle} - Y_i] - \beta \frac{\partial}{\partial \mu_j} U(\mu^n)}{\sum_i Y_i l_{ij} + \beta \mu_j^n \frac{\partial^2}{\partial \mu_j^2} U(\mu^n)};$$

wherein $\beta$ is an optimization parameter, $$\langle l_i, \mu \rangle = \sum_j l_{ij} \mu_j, \quad \overline{\sum_i Y_i l_{ij}}$$

is the average value over all voxels of the volume element across all i and j, $Y_i$ is the measured photon count in the projection i and $l_{ij}$ is the section length of the beam through the voxel j in the projection i, and wherein $\beta$ is determined by means of the following equation:

$$\beta = \frac{\Delta\tilde{\mu} \cdot \overline{\sum_i Y_i l_{ij}}}{\overline{\mu} \cdot \frac{\partial}{\partial \mu_j} U(\mu)\bigg|_{\Delta\mu_j = \Delta\tilde{\mu}} - \Delta\tilde{\mu} \cdot \overline{\mu} \cdot \frac{\partial^2}{\partial \mu_j^2} U(\mu)\bigg|_{\Delta\mu_j = \Delta\tilde{\mu}}};$$

this formula is derived from the aforementioned update formula to determine $\mu_j$, wherein the target function $L(\mu)$ and the equation for $\phi(\mu)$ described above were used in the equation.

The control parameter $\beta$ can be determined before the first iteration with the assistance of the Geman prior function $U(\mu)$. However, the difference of adjacent attenuation coefficients $\Delta\mu_{jk}$ is not yet known at this point in time. If the measurement data are determined by means of x-ray radiation, it can be assumed that the noise in a projection is constant. In this case the expression $\Delta\mu_{jk}$ is therefore replaced by the maximum noise value $\Delta\tilde{\mu}$. If the measurement data were generated by a magnetic resonance scanner (data acquisition unit), the noise can be spatially dependent, so the expression $\Delta\mu_{jk}$ in the Geman prior function $U(\mu)$ can be replaced with a spatially dependent estimated noise value $\Delta\tilde{\mu}_j$. As noted, the $\mu_j$ values and the difference of the attenuation coefficients $\Delta\mu_{jk}$ can be determined beforehand via conventional back-projection methods. $\beta$ thus can be determined with more precision.

As an alternative, the reconstruction method can use an iterative, convex optimization updating formula. For this the step of the iterative calculation of the estimated value of the attenuation coefficient $\mu_j$ of a voxel j is implemented by means of the following equation:

$$\mu_j^{n+1} = \mu_j^n + \mu_j^n \frac{\sum_i l_{ij}[d_i e^{-\langle l_i, \mu \rangle} - Y_i] - \beta \frac{\partial}{\partial \mu_j} U(\mu^n)}{\sum_i l_{ij} \langle l_i, \mu^n \rangle d_i e^{-\langle l_i, \mu^n \rangle} + \beta \mu_j^n \frac{\partial^2}{\partial \mu_j^2} U(\mu^n)};$$

wherein $\beta$ is an optimization parameter, $$\langle l_i, \mu \rangle = \sum_j l_{ij} \mu_j,$$

is the average value over all voxels of the volume element across all i and j, $Y_i$ is the measured photon count in the projection i and $l_{ij}$ is the section length of the beam through the voxel j in the projection i, and wherein β is determined before iterations by means of the following formula:

$$\beta = \frac{\Delta\tilde{\mu} \cdot \sum_i l_{ij}\langle l_i, \overline{\mu}\rangle d_i e^{-\langle l_i, \overline{\mu}\rangle}}{\overline{\mu} \cdot \frac{\partial}{\partial \mu_j} U(\mu)\bigg|_{\Delta\mu_j = \Delta\tilde{\mu}} - \Delta\tilde{\mu} \cdot \overline{\mu} \cdot \frac{\partial^2}{\partial \mu_j^2} U(\mu)\bigg|_{\Delta\mu_j = \Delta\tilde{\mu}}};$$

wherein $\langle l_i, \overline{\mu}\rangle = \sum_j l_{ij}\mu_j$.

However, the difference of adjacent attenuation coefficients $\Delta\mu_{jk}$ is not yet known at this point in time. If the measurement data are determined by means of x-ray radiation, it can be assumed that the noise in a projection is constant. In this case the expression $\Delta\mu_{jk}$ is therefore replaced by $\Delta\tilde{\mu}$. If the measurement data were generated by means of a magnetic resonance tomograph, the noise can be spatially dependent, whereby the expression $\Delta\mu_{jk}$ in the Geman prior function $U(\mu)$ can be replaced with a spatially dependent estimated noise values $\Delta\tilde{\mu}_j$. As noted, the difference of the attenuation coefficients $\Delta\mu_{jk}$ can be determined beforehand via conventional back-projection methods. β can thereby be determined with more precision.

The determined attenuation coefficients $\mu_j$ are shown on a display device (for example a monitor) as grey values or in a false color representation. The determined attenuation coefficients can also be shown, for example as intensities or false colors.

The described method can also be used to improve contrast in the event that a three-dimensional reconstruction was computed beforehand, for example via an unfiltered or filtered back-projection. The unfiltered back-projection provides initialization values $\mu_j^0$ so that a faster convergence can be achieved.

The invention also concerns a tissue density determination device with an emitter that emits radiation into a tissue and a detector that detects the radiation after it has traversed the tissue. The tissue density determination device comprises a noise value estimation device that is fashioned to estimate the estimated noise value $\Delta\tilde{\mu}$ of the voxel attenuation coefficients $\mu$. The noise value estimation device is configured to determine the expected noise value $\Delta\tilde{\mu}$ of the voxel attenuation coefficients μ from the tissue density and the information about the emitted radiation, in particular from the breast thickness and the tube charge (mAs). The noise level can generally be kept constant for an arbitrary breast thickness via selection of the tube charge and the photon energy (keV). The estimated noise value $\Delta\tilde{\mu}$ must be less than the least gradient to be preserved. The estimated noise value $\Delta\tilde{\mu}$ is the maximum estimated noise value that is expected in an image if no smoothing takes place.

The tissue density determination device can also comprise a tissue attenuation average value estimation device that is fashioned to estimate an average tissue attenuation coefficient $\overline{\mu}$, wherein the tissue attenuation average value estimated value device advantageously determines the average tissue attenuation coefficient $\overline{\mu}$ on the basis of a tissue density attenuation and the energy of the radiation emitted by the emitter. For example, the estimated tissue attenuation value $\overline{\mu}$ can be determined from the photon energy and the breast density that is estimated from segmented original projections using existing methods. The expected noise value $\Delta\tilde{\mu}$ and/or the estimated average tissue attenuation value $\overline{\mu}$ can be determined by means of commonly used regression methods.

The tissue density determination device can also have a prior function determination device that is fashioned to calculate parameters of a prior function $U(\mu)$ from the estimated noise value $\Delta\tilde{\mu}$ and the averaged tissue attenuation coefficient $\overline{\mu}$. The tissue density determination device also comprises an iteration device that is fashioned to calculate the expected value of an attenuation coefficient $\mu_j$ of a voxel j from projection data detected by means of the detector (18), the estimated noise value $\Delta\tilde{\mu}$, the average estimated tissue attenuation value $\overline{\mu}$ and the prior function $U(\mu)$. The estimated noise value $\Delta\tilde{\mu}$ is that noise value that is expected in an image if no smoothing has taken place.

The determined attenuation coefficient $\mu_j$ can be represented on a display device as a grey value or in false color. It is thus possible to differentiate denser tissue from less dense tissue since the attenuation coefficient increases with the tissue density, while a higher signal-to-noise ratio and contrast/noise ratio is achieved than with methods of the prior art. Due to the improved signal-to-noise ratio and contrast/noise ratio, the radiation dose can be reduced, whereby the side effects are reduced.

The prior function determination device can be fashioned to calculate the parameters of a Geman prior function. The Geman prior function $U(\mu)$ can have the following equation:

$$U(\mu) = \sum_j \sum_k \frac{\Delta\mu_{jk}^2 \sigma^m}{2\left(\sqrt{\Delta\mu_{jk}^2/2 + \sigma^2/2}\right)^m};$$

wherein σ is an optimization parameter and m is a constant, and wherein $\mu_k$ and $\mu_j$ are attenuation coefficients of adjacent voxels that are associated with a respective tissue segment and j and k are linear voxel indices over three dimensions. The values of the attenuation coefficients $\mu_k$ and $\mu_j$ are updated with each iteration. This means that these values are prepopulated with estimated values in the first iteration, for example with the average tissue attenuation value. In the subsequent iterations those values that were determined in the preceding iteration are used for the attenuation coefficients $\mu_k$ and $\mu_j$. For example, a neighborhood of 3×3×3 voxels can be evaluated.

Before the image was reconstructed, the differences of the attenuation coefficients $\Delta\mu_{jk}$ were not known. If the reconstruction method is applied to data that were generated by means of x-rays, it is assumed that the noise in the projection is spatially independent. Therefore, to determine the optimal value for the σ value in the Geman prior function, the term $\Delta\mu_{jk}$ is replaced by the estimated noise value $\Delta\tilde{\mu}$, corresponding to the maximum estimated noise value.

If the image data were acquired by means of a magnetic resonance tomograph, the noise can be spatially dependent. In this case the value $\Delta\tilde{\mu}_j$ can be dependent on the location of the voxel j.

However, it is also possible to determine the values $\mu_j$ and $\mu_k$—and thus $\Delta\mu_{jk}$—by means of conventional reconstruction methods, for example by means of a linear and/or filtered back-projection. σ thus can be determined more precisely.

The tissue density determination device is fashioned such that—in the event that the Geman prior function should have a convex shape—σ is selected so that the first derivative of the Geman prior function reaches its highest curvature at values of $\Delta\mu$ that correspond to that at the estimated noise value $\Delta\tilde{\mu}$, and m is ≦16/17. The Geman prior function determination device is fashioned such that—in the event that the Geman prior function should have a non-convex shape—σ is selected so that the first derivative of the Geman prior function reaches its maximum at values of Δμ that correspond to the estimated noise value $\Delta\tilde{\mu}$, and m is, for example, 2.

The iteration device is fashioned to determine the estimated value of the attenuation coefficients of a voxel for three-dimensional image reconstruction by means of the following maximum a posteriori method, which is a Newton-based updating method with a simple quadratic smoothing prior function $U(\mu)$:

$$\mu_j^{n+1} = \mu_j^n + \frac{\mu_j^n}{\sum_i Y_i l_{ij} + \beta \mu_j^n \frac{\partial^2}{\partial \mu_j^2} U(\mu^n)} \frac{\partial}{\partial \mu_j} \Phi(\mu^n);$$

wherein β is an optimization parameter, $\phi(\mu^n) = L(\mu) - \beta U(\mu)$, $L(\mu)$ is a target function, $Y_i$ is the measured photon count in the projection i and $l_{ij}$ is the section length of the beam through the voxel j in the projection i. The initial value $\mu_j^0$ of the iterative method can be selected as has been stated in the preceding with regard to the method.

The goal function $L(\mu)$ can be stated as follows:

$$L(\mu) = \sum_i \{-d_i e^{-\langle l_i, \mu \rangle} - Y_i \langle l_i, \mu \rangle\} + c;$$

wherein $\langle l_i, \mu \rangle = \sum_j l_{ij} \mu_j$, i is a projection index, j is the voxel index, $d_i$ is the expected photon count that exits from the radiation source along the projection i, $Y_i$ is the detected photon count in the projection i and c is a constant.

The iteration device can be fashioned to determine β by means of the following formula:

$$\beta = \frac{\Delta\tilde{\mu} \cdot \overline{\sum_i Y_i l_{ij}}}{\overline{\mu} \cdot \frac{\partial}{\partial \mu_j} U(\mu)\bigg|_{\Delta\mu_j=\Delta\tilde{\mu}} - \Delta\tilde{\mu} \cdot \overline{\mu} \cdot \frac{\partial^2}{\partial \mu_j^2} U(\mu)\bigg|_{\Delta\mu_j=\Delta\tilde{\mu}}};$$

wherein $\overline{\sum_i Y_i l_{ij}}$ is the average value across all voxels of the volume element across all i and j.

However, the difference between adjacent attenuation coefficients $\Delta\mu_{jk}$ is not yet known at this point in time. If the measurement data are determined by means of x-ray radiation, it can be assumed that the noise in a projection is constant. In this case the expression $\Delta\mu_{jk}$ is replaced with $\Delta\tilde{\mu}$. If the measurement data were generated by means of a magnetic resonance tomograph, the noise can be spatially dependent, whereby the expression $\Delta\mu_{jk}$ in the Geman prior function $U(\mu)$ can be replaced by a spatially-dependent estimated spatial values $\Delta\tilde{\mu}_j$. As was previously mentioned, the difference of the attenuation coefficients $\Delta\mu_{jk}$ can be determined beforehand via conventional back-projection methods, whereby β can be determined more precisely.

The iteration device can be fashioned to implement the three-dimensional reconstruction by means of an iterative gradient optimization updating formula. The iterative calculation of the estimated value of the attenuation coefficient $\mu_j$ of a voxel j can hereby be implemented by means of the following formula:

$$\mu_j^{n+1} = \mu_j^n + \mu_j^n \frac{\sum_i l_{ij}[d_i e^{-\langle l_i, \mu \rangle} - Y_i] - \beta \frac{\partial}{\partial \mu_j} U(\mu^n)}{\sum_i Y_i l_{ij} + \beta \mu_j^n \frac{\partial^2}{\partial \mu_j^2} U(\mu^n)};$$

wherein β is an optimization parameter, $$\langle l_i, \mu \rangle = \sum_j l_{ij} \mu_j, \quad \overline{\sum_i Y_i l_{ij}}$$

is the average value across all voxels of the volume element over all i and j, $Y_i$ is the measured photon count in the projection i and $l_{ij}$ is the section length of the beam through the voxel j in the projection i, and wherein β is determined by means of the following formula:

$$\beta = \frac{\Delta\tilde{\mu} \cdot \overline{\sum_i Y_i l_{ij}}}{\overline{\mu} \cdot \frac{\partial}{\partial \mu_j} U(\mu)\bigg|_{\Delta\mu_j=\Delta\tilde{\mu}} - \Delta\tilde{\mu} \cdot \overline{\mu} \cdot \frac{\partial^2}{\partial \mu_j^2} U(\mu)\bigg|_{\Delta\mu_j=\Delta\tilde{\mu}}};$$

this formula corresponds to the aforementioned formula to determine $\mu_j$, wherein the target function $L(\mu)$ and the Equation for $\phi(\mu)$ explained above were used.

The control parameter β can be determined before the first iteration based on the Geman prior function $U(\mu)$. However, at this point in time the difference of adjacent attenuation coefficients $\Delta\mu_{jk}$ is not yet known. If the measurement data are determined by means of x-ray radiation, it can be assumed that the noise in a projection is constant. In this case the expression $\Delta\mu_{jk}$ is therefore replaced with $\Delta\tilde{\mu}$. If the measurement data were generated by means of a magnetic resonance scanner, the noise can be spatially dependent, whereby the expression $\Delta\mu_{jk}$ in the Geman prior function $U(\mu)$ can be replaced with a spatially dependent estimated noise values $\Delta\tilde{\mu}$. As was previously mentioned, the difference of the attenuation coefficients $\Delta\mu_{jk}$ can be determined via conventional back-projection methods, so β can be determined more precisely.

As an alternative to this, the iteration device can be fashioned to implement the three-dimensional reconstruction by means of an iterative convex optimization updating formula. For this the iterative calculation of the estimation value of the attenuation coefficient $\mu_j$ of a voxel j is implemented by means of the following formula:

$$\mu_j^{n+1} = \mu_j^n + \mu_j^n \frac{\sum_i l_{ij}[d_i e^{-\langle l_i, \mu \rangle} - Y_i] - \beta \frac{\partial}{\partial \mu_j} U(\mu^n)}{\sum_i l_{ij}\langle l_i, \mu^n \rangle d_i e^{-\langle l_i, \mu^n \rangle} + \beta \mu_j^n \frac{\partial^2}{\partial \mu_j^2} U(\mu^n)};$$

wherein β is an optimization parameter, $$\langle l_i, \mu \rangle = \sum_j l_{ij} \mu_j,$$

is the average value across all voxels of the volume element over all i and j, $Y_i$ is the measured photon count in the projection i and $l_{ij}$ is the section length of the beam through the voxel j in the projection i, and wherein β is determined by means of the following formula:

$$\beta = \frac{\Delta\tilde{\mu} \cdot \sum_i l_{ij}\langle l_i, \overline{\mu}\rangle d_i e^{-\langle l_i, \overline{\mu}\rangle}}{\overline{\mu} \cdot \frac{\partial}{\partial \mu_j}U(\mu)\bigg|_{\Delta\mu_j=\Delta\tilde{\mu}} -\Delta\tilde{\mu} \cdot \overline{\mu} \cdot \frac{\partial^2}{\partial \mu_j^2}U(\mu)\bigg|_{\Delta\mu_j=\Delta\tilde{\mu}}};$$

wherein $l_{ij}$ is the intersection length of the beam through the voxel j in the plane i, $\langle l_{ij}\overline{\mu}\rangle$ is the average value across all voxels of the volume element over all j and i.

The control parameter β can be determined before the first iteration based on the Geman prior function U(μ) and the update function. However, at this point in time the difference of adjacent attenuation coefficients $\Delta\mu_{jk}$ is not yet known. If the measurement data are determined by means of x-ray radiation, it can be assumed that the noise in a projection is constant. In this case the expression $\Delta\mu_{jk}$ is therefore replaced with $\Delta\tilde{\mu}$. If the measurement data were generated by means of a magnetic resonance tomograph, the noise can be spatially dependent, so the expression $\Delta\mu_{jk}$ in the Geman prior function U(μ) can be replaced with a spatially dependent estimated noise values $\Delta\tilde{\mu}_j$. As was previously mentioned, the difference of the attenuation coefficients $\Delta\mu_{jk}$ can be determined via conventional back-projection methods in order to parameterize β more precisely.

The invention also concerns a computer-readable storage medium encoded with program code that can be loaded into a computer, the program code causing all steps of the previously described method.

The invention also concerns a medical system with the previously described tissue density determination device and positioning arrangement in order to establish at least one part of an organ of a patient spatially relative to the emitter and the detector, and a display device that is fashioned to display representation of the values $\mu_j$. The organ can be the breast or any other organ or portion of the body. The display device can be a monitor or a printer. The representations of the tissue attenuation coefficients can be intensities, grey values or false colors.

DESCRIPTION OF THE PREFERRED EMBODIMENTS

Figure 1:
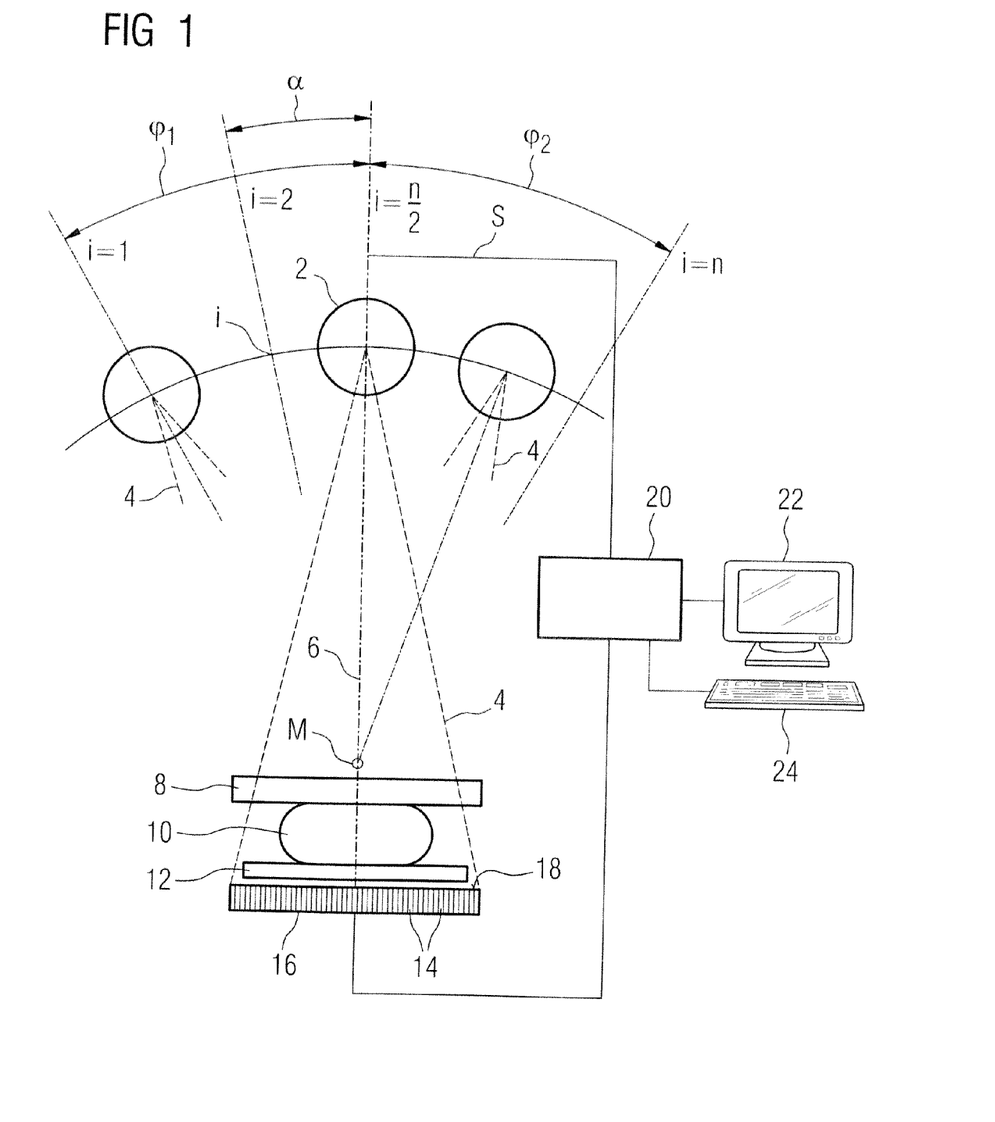
FIG. 1 shows an x-ray apparatus that is operable in accordance with the invention.

FIG. 1 shows a mammography apparatus as an embodiment of an x-ray apparatus. The mammography apparatus has a pannable x-ray tube 2 that generates x-rays 4. The x-ray tube 2 can be panned by an angle α around the center point M within an angle range from $-\phi_1$ to $+\phi_2$. An angle α of the x-ray tube relative to the axis of symmetry 6 is associated with each projection i. The mammography apparatus has a compression plate 8 and a detector or plate 12 between which the organ 10 to be examined (i.e. the female breast) is placed for examination. The x-ray apparatus has a detector 18 with a number of measurement elements 14, 16 that are arranged like a matrix on the detector 18.

To acquire a two-dimensional projection, the x-ray tube 2 is panned into the first position i=1. An x-ray beam 4 is subsequently generated that runs through the compression plate 8, 12 and through the organ 10 to be examined and is detected by the measurement elements 14, 16 of the detector 18. The x-ray tube 2 is panned in the second position i=2 and once again an x-ray beam 4 is generated that runs through the organ 10 to be examined from a different angle and consequently passes through in a different projection i. The x-rays are detected by the measurement elements 14, 16 of the detector 18 after passing through organ 10 to be examined. The mammography apparatus can acquire n projections of the organ 10 to be examined. The number of acquired projections n could be, for example, in a range from 20 to 50 projections.

The two-dimensional projections are converted by the tissue density determination device 20 into a three-dimensional representation. A section through the three-dimensional representation that is shown on the display device 22 can be selected by means of the keyboard 24.

Figure 2:
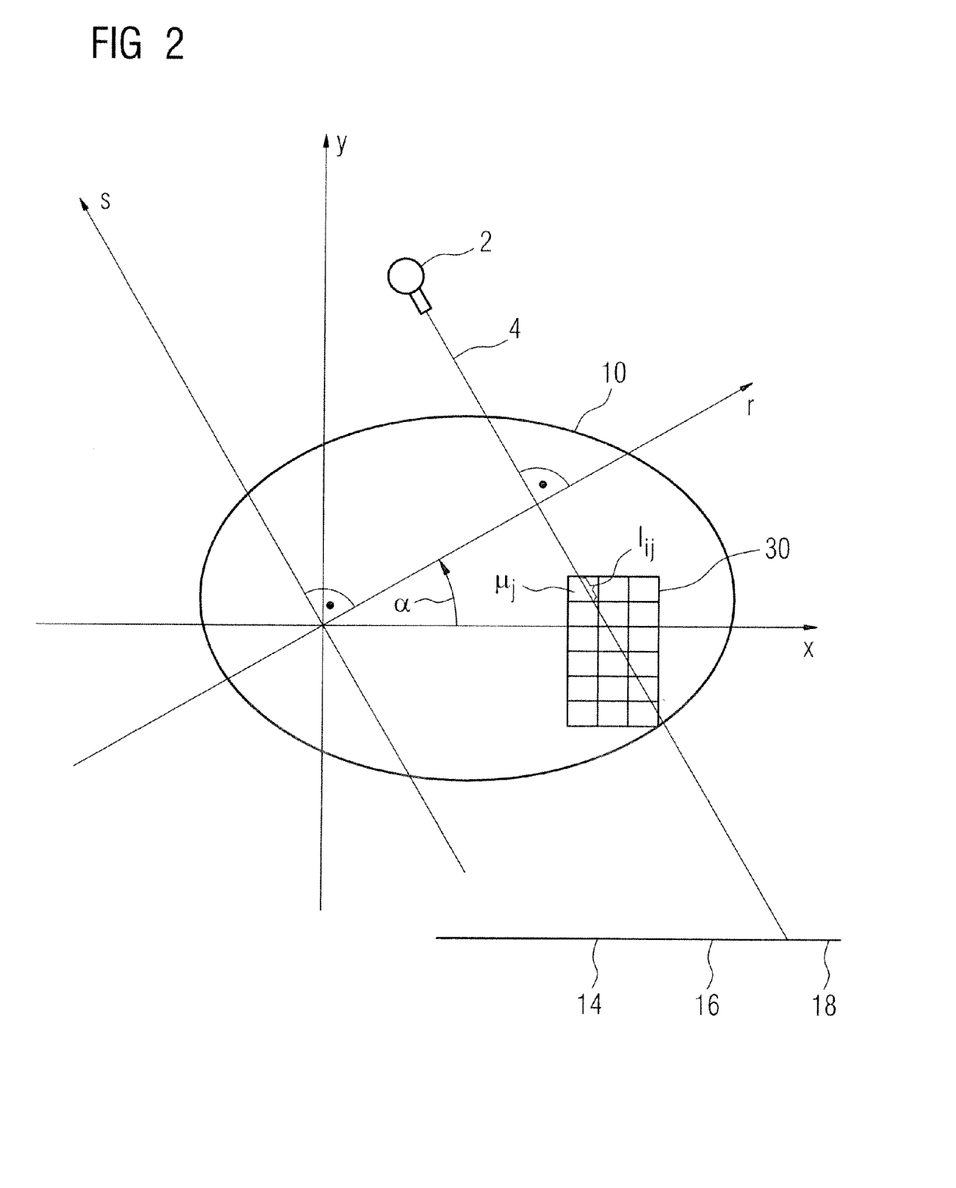
FIG. 2 shows the physical basis of the attenuation of x-ray radiation in tissue.

Reference is made to FIG. 2 in order to explain the physical basis of the determination of the radiographic tissue density by means of x-rays.

The basis for measurement of tissue by means of x-ray radiation are explained in detail in Imaging Systems for Medical Diagnostics, Arnulf Oppelt, Publicis Corporate Publishing, Erlangen, ISBN 3-89578-226-4, Chapters 9 and 10.

The x-ray tube 2 emits an x-ray beam 4 that is detected by the detector 18. The x-ray beam 4 is attenuated in the tissue 10. Each tissue element 30 that is represented as a voxel on the display device 22 has an individual attenuation coefficient $\mu_j$. The intensity detected by the respective measurement element 14, 16 of the detector 18 can be calculated as follows:

$$J(r,\phi)=J_0 \cdot e^{-\int \mu ds}$$

The intensity J detected by the respective measurement element 14, 16 of the detector 18 can be represented with discrete equation:

$$J(r,\phi)=J_0 \cdot e^{-\Sigma_{j=z^j} l_{ij}\mu_j};$$

wherein $\mu_j$ is the attenuation coefficient of a tissue segment or voxel, $J_0$ is the intensity of the x-ray beam before the entrance into the tissue, i is the respective projection, j is the voxel index and $l_{ij}$ is the intersection length. The intersection length $l_{ij}$ consequently designates the length through which the x-ray beam traverses the voxel j with the attenuation coefficient μ.

As described above, the x-ray tube 2 is panned by an angle α in order to subsequently acquire additional two-dimensional projections that are subsequently additionally processed into a three-dimensional image by the tissue density determination device 22.

The attenuation coefficient $\mu_j$ correlates with the tissue density. As was mentioned above, the female breast comprises glandular tissue, adipose tissue, connective tissue and blood vessels, the x-ray attenuation coefficients of which are very similar. Adding difficulty to this is that the x-ray attenuation coefficient of cancerous tissue has similar x-ray attenuation coefficients as the aforementioned tissue types. A particularly low-noise reconstruction method must consequently be provided for tomosynthesis in the field of mammography, which moreover clearly shows the edges and boundaries of the aforementioned tissue types.

The detector determines the intensity of the beam 4 by means of the measurement elements 14 and 16 arranged like a matrix. A measurement element 14, 16 cannot show the tissue attenuation coefficient $\mu_j$ but rather only determine a value that indicates how strongly the x-ray beam 4 was attenuated or, respectively, weakened in the tissue 10 the initial intensity $I_0$ of the x-ray beam is known. However, since multiple projections i are acquired from different angles $\alpha$ of the tissue 10, wherein the tissue 10 remains fixed, it is possible to determine a three-dimensional image in the tissue attenuation value determination device 20.

Figure 3:
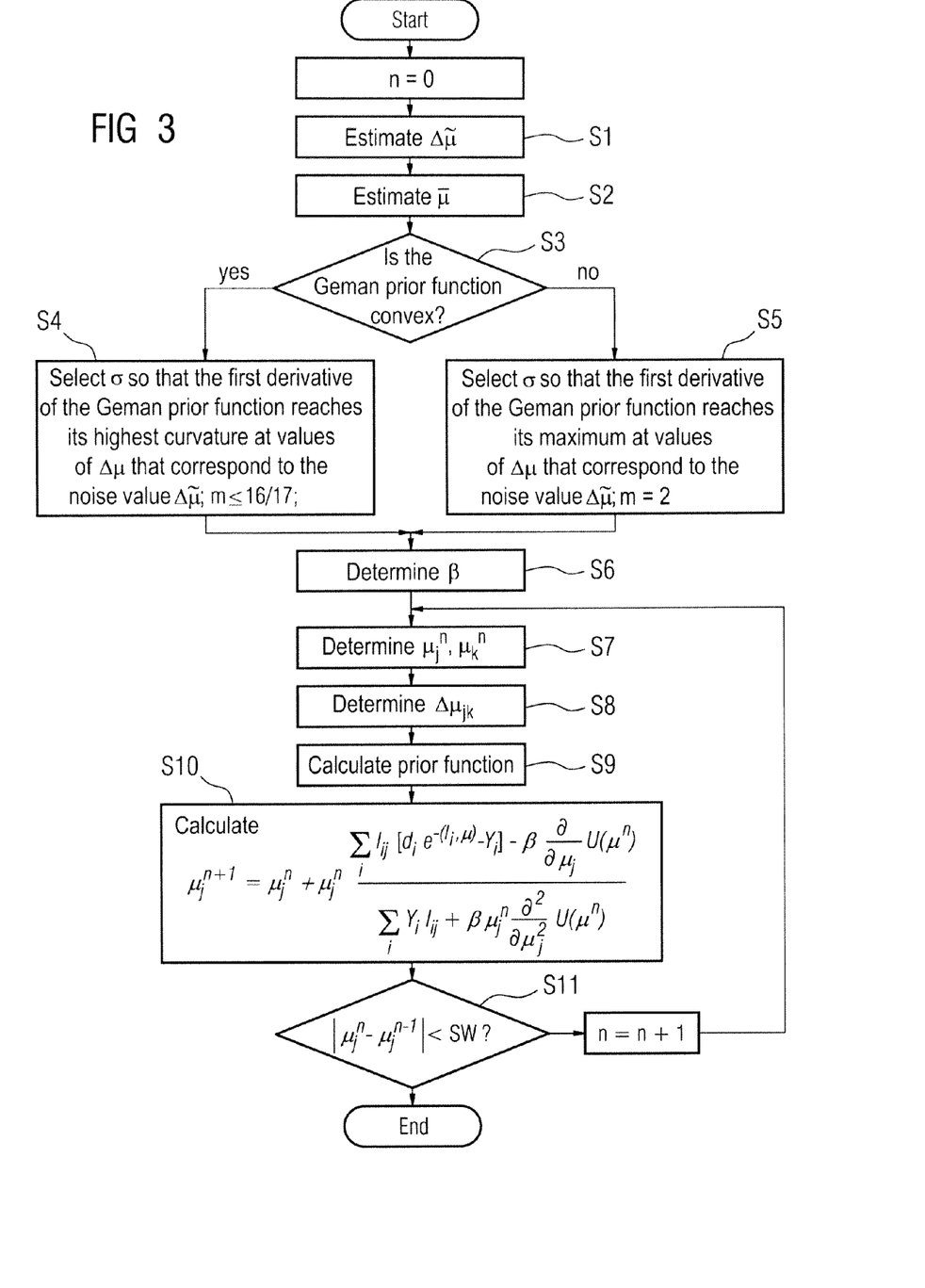
FIG. 3 is a flow chart of an embodiment of the method according to the invention.

After a number of two-dimensional images have been determined in different projections i, the reconstruction method according to the invention is now described in detail with reference to FIG. 3.

At the start of the iteration method the iteration index n is 0. In Step S1 the estimated noise value $\Delta\tilde{\mu}$ of the attenuation coefficient $\mu$ of a voxel is estimated. The estimation takes place in a given x-ray spectrum as a function of the breast thickness and the tube charge (mAs) using regression methods and previously implemented statistical tests. In general the noise level for an arbitrary breast thickness can be kept constant via selection of the rube charge and the photon energy (keV). The estimated noise value $\Delta\tilde{\mu}$ must be less than the smallest gradient to be obtained. The estimated noise value $\Delta\tilde{\mu}$ is the maximum noise value that is expected in an image if no smoothing by means of a prior function takes place.

The method subsequently continues with Step S2. In Step S2 the average estimated tissue attenuation value or, respectively, estimated average tissue attenuation coefficient $\bar{\mu}$. The estimated average tissue attenuation coefficient $\bar{\mu}$ is estimated using regression methods and statistical tests from the photon energy and the breast density estimation. The estimated tissue attenuation coefficient can also be obtained from segmented original projections using known methods from photon energy and breast thickness estimation. Such methods are, for example, described in O. Alonzo-Proulx, A. H. Tyson, G. E. Marwdsley, M. J. Yaffe, Effect of Tissue Thickness Variation in Volumetric Breast Density Estimation, Proc. IWDM 2008, pp. 659-666. The estimated noise value $\Delta\tilde{\mu}$ and the breast density can be calculated from the segmented reconstructed breast volume $\mu^0$ that is used for initialization.

In Step S3 it is subsequently checked whether the Geman prior function should be convex. The following Equation is used as a Geman prior function $U(\mu)$:

$$U(\mu) = \sum_j \sum_k \frac{\Delta\mu_{jk}^2 \sigma^m}{2\left(\sqrt{\Delta\mu_{jk}^2/2 + \sigma^2/2}\right)^m};$$

wherein $\sigma$ is an optimization parameter and m is a constant.

Before the image was reconstructed, the differences $\Delta\mu_{jk}$ are not known. If the reconstruction method is applied to data that were generated by means of x-rays, it is assumed that the noise in the projection is spatially independent. Therefore, to determine the optimal value for the value $\sigma$ in the Geman prior function the term $\Delta\mu_{jk}$ is replaced with the estimated noise value $\Delta\tilde{\mu}$, by the maximum estimated noise value.

However, it is also possible to determine the values $\mu_j$ and $\mu_k$ (and thus $\Delta\mu_{jk}$) by means of conventional reconstruction methods, for example by means of a linear and/or filtered back-production [sic]. The parameter $\sigma$ can hereby be determined more precisely.

It is preferred that the Geman prior function has a convex shape in order to ensure the convergence while the noise is suppressed.

If it was established in Step S3 that the Geman prior function should be convex, the workflow proceeds to Step S4. $\sigma$ is selected so that the first derivative of the Geman prior function reaches its highest curvature at values of $\Delta\tilde{\mu}$ that correspond to the expected noise level. The constant m is established as follows: $m \leq 16/17$.

If it was established in Step S3 that the Geman prior function should not be convex, the workflow proceeds to Step S5. $\sigma$ is hereby selected so that the first derivative of the Geman prior function reaches its maximum at values of $\Delta\tilde{\mu}$ that correspond to the expected noise level. The constant m could be, for example, 2.

After Step S4 or S5, the method proceeds with Step S6 and determines the control parameter $\beta$. The control parameter $\beta$ is always greater than 0. The control parameter $\mu$ is determined before the first iteration by means of the following formula:

$$\beta = \frac{\Delta\tilde{\mu} \cdot \overline{\sum_i Y_i l_{ij}}}{\bar{\mu} \cdot \frac{\partial}{\partial \mu_j} U(\mu)\bigg|_{\Delta\mu_j = \Delta\tilde{\mu}} - \Delta\tilde{\mu} \cdot \bar{\mu} \cdot \frac{\partial^2}{\partial \mu_j^2} U(\mu)\bigg|_{\Delta\mu_j = \Delta\tilde{\mu}}};$$

wherein $l_j$ is the section length of the beam through the voxel j in the plane i, $$\sum_i Y_i l_{ij}$$

is the average value across all voxels of the volume over all j and i.

The determination of the section length $l_{ij}$ was previously explained using FIG. 2. $Y_i$ is the measured photon count in the projection i.

However, at this point in time the difference of adjacent attenuation coefficients $\Delta\mu_{jk}$ is not yet known. If the measurement data are determined by means of x-ray radiation, it can be assumed that the noise in a projection i is constant. In this case the expression $\Delta\mu_{jk}$ is therefore replaced with $\Delta\tilde{\mu}$. If the measurement data were generated by means of a magnetic resonance tomograph, the noise can be spatially dependent, whereby the expression $\Delta\mu_{jk}$ in the Geman prior function can be replaced with a spatially dependent estimated noise values $\Delta\tilde{\mu}$. As was previously mentioned, the difference of the attenuation coefficients $\Delta\mu_{jk}$ can be determined beforehand via conventional back-projection methods.

In Step S7 the attenuation coefficients $\mu_j^n$ and $\mu_k^n$ are subsequently determined that are associated with adjacent voxels. The indices j and k are linear indices across three dimensions. The values of the attenuation coefficients $\mu_j^n$ and $\mu_k^n$ can be those that were determined in a preceding iteration. These attenuation coefficients can be initialized in the first iteration with an estimated value that is identical for all voxels, for example. The attenuation coefficients $\mu_j^n$ and $\mu_k^n$ can also be determined by means of conventional three-dimensional reconstruction methods in order to accelerate the convergence. In Step S8 the differences of the index $\Delta\mu_{jk}$ are subsequently calculated. It applies that:

$$k \in N_j;$$

the difference $\Delta\mu_{jk}$ can be determined in a neighborhood of 3×3×3 voxels, for example.

Step S9, which is executed after Step S8, determines the Geman prior function from $\Delta\mu_{jk}$, σ, m, j and k. The Geman prior function $U(\mu)$ is used as a smoothing prior function that penalizes differences in values of adjacent pixels.

After Step S9, the method proceeds with Step S10. In Step S10 the attenuation coefficient $\mu_j$ is iteratively determined via a maximum A posterior method that uses a Newton-based updating method with a simple quadratic smoothing prior function $U(\mu)$.

The equation of the iterative maximum A posterior method reads as follows:

$$\mu_j^{n+1} = \mu_j^n + \mu_j^n \frac{\sum_i l_{ij}[d_i e^{-\langle l_i, \mu \rangle} - Y_i] - \beta \frac{\partial}{\partial \mu_j} U(\mu^n)}{\sum_i Y_i l_{ij} + \beta \mu_j^n \frac{\partial^2}{\partial \mu_j^2} U(\mu^n)}$$

wherein $\langle l_i, \mu \rangle = \sum_j l_{ij} \mu_j$, $d_i$ is the expected photon count that escapes from the radiation source along the projection i, β is the optimization parameter, $Y_i$ is the measured photon count in the plane i, n is the iteration parameter and $l_{ij}$ is the section length of the beam through the voxel j in the plane i.

The initial value $\mu_j^0$ can be initialized with a uniform value for all voxels. For example, the initial value can be established at the average attenuation value or, respectively, attenuation coefficients of the breast tissue. A faster convergence can be achieved in the event that that initial value is established with a value that was determined by means of a normalized back-projection method.

In Step S11 that follows Step S10, it is checked whether $\mu_j$ has varied in the last iteration by a difference that is smaller than a threshold. In the event that the variation of $\mu_j$ is not less than a threshold, the iteration parameter n is incremented by 1, the method returns to Step S3 and an additional iteration is implemented. In the event that the change of $\mu_j$ in the last iteration is less than a predetermined threshold, the method is ended and $\mu_j$ is determined with sufficient precision.

Figure 4:
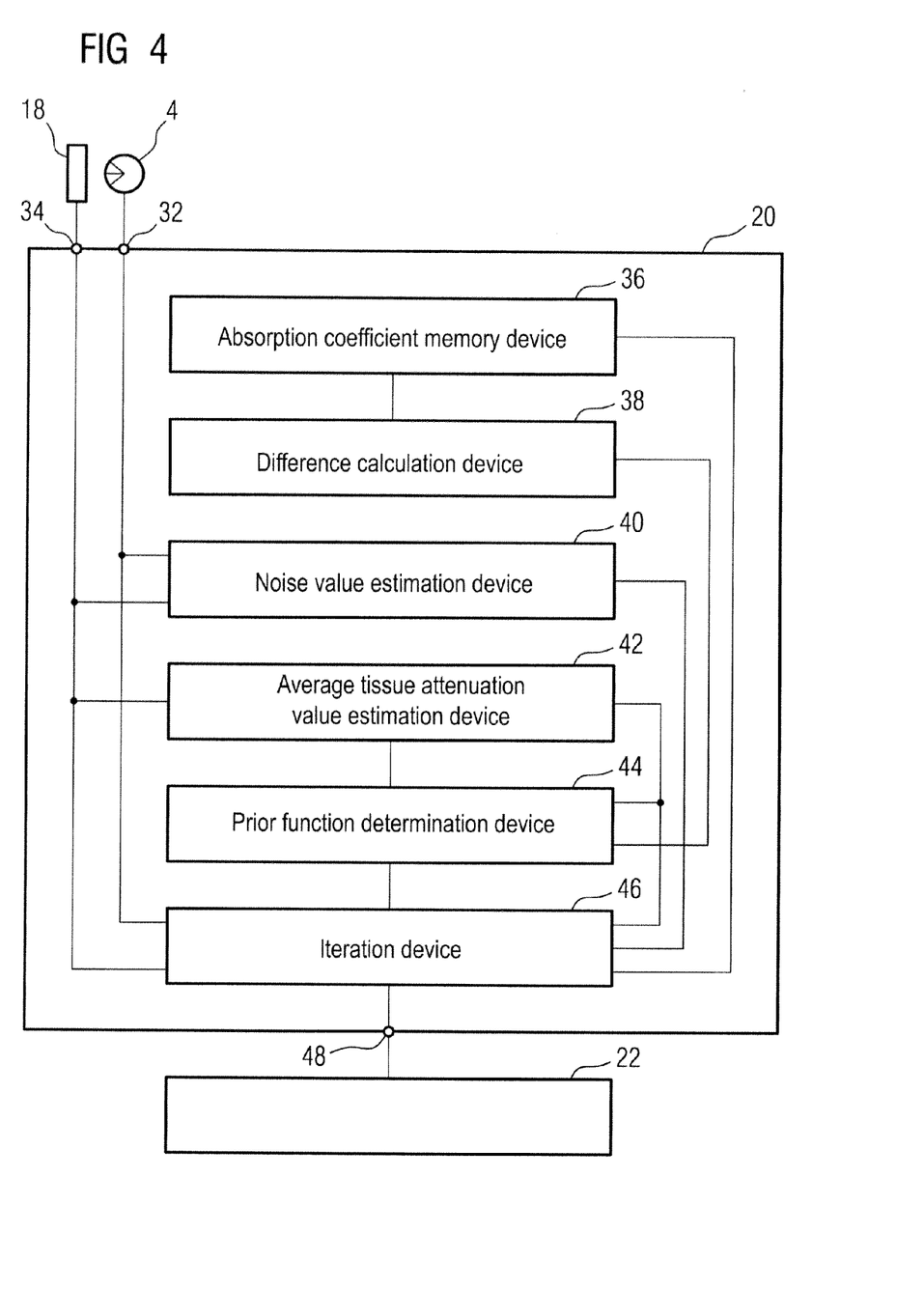
FIG. 4 illustrates details of a tissue attenuation value determination device according to the invention.

FIG. 4 shows details of the tissue density determination device 20. Via an input port 32, the tissue density determination device 20 receives data from the x-ray tube 4, for example the tube charge, the expected photon count $d_i$, the intensity of the x-ray beam upon exit from the x-ray tube etc. Via a second port 34, the tissue density determination device 20 receives data from the detector 18, for example the received intensity of the x-ray beam at the respective measurement elements 14, 16 arranged like a matrix.

The tissue density determination device 20 has an attenuation coefficient memory device 36 that executes the previously described Step S7 and stores attenuation coefficients $\mu_j$ and $\mu_k$. A difference calculation device 38 of the tissue density determination device 20 executes the previously described Step S8. The tissue density determination device 20 also has a noise value estimation device 40 that executes the previously described Step S1. Step S2 is executed by a tissue attenuation average value estimation device 42 of the tissue density determination device 20. A prior function estimation device 44 of the tissue density determination device 20 is fashioned to execute Steps S3, S4, S5 and S9. An iteration device 46 of the tissue density determination device 20 leads to Steps S6, S10 and S11. The determined attenuation coefficients $\mu_j$ are output via a third connection 48 of the tissue density determination device 20 to a display device 22.

It is understood that the tissue density determination device 20 can be made up of discrete components. The tissue density determination device 20 can also be implemented by a computer that is fashioned to execute the method described with reference to FIG. 3, which method is implemented in a computer program product.

The method according to the invention reduces the noise and improves the signal-to-noise ratio and the contrast/noise ratio.

| Method | Noise level at a feature-less point - standard deviation | Signal/noise ratio | Contrast/noise ratio |
|---|---|---|---|
| Filtered back-projection | 1.59% | 59.35 | 2.27 |
| Maximum likelihood method without prior functions | 1.35% | 61.41 | 2.04 |
| Maximum a posteriori method with Geman prior function | 0.63% | 171.46 | 4.80 |

Due to the improved signal-to-noise ratio and the improved contrast/noise ratio, a lower radiation dose can be used which reduces the side effects of the diagnostic imaging.

Figure 5:
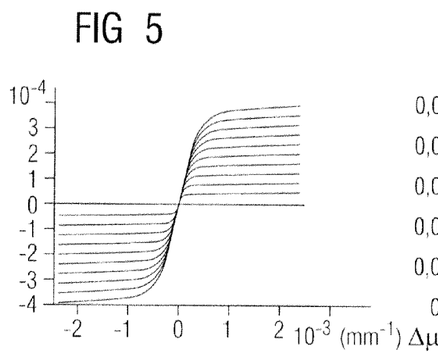
FIGS. 5 and 6 respectively show the first and second derivatives of the Geman prior function.
Figure 6:
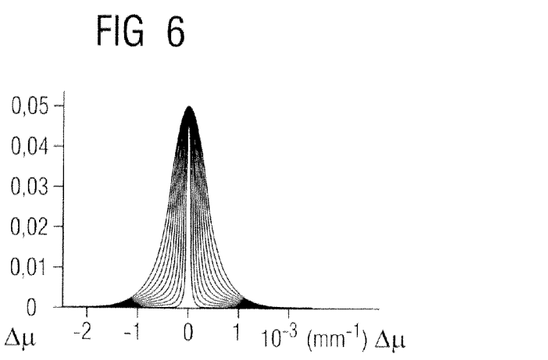

FIG. 5 shows the first derivative of the Geman prior function for $0 < \sigma \leq 0.0006$. FIG. 6 shows the second derivative of the Geman prior function that is positively definite throughout.

Figure 7:
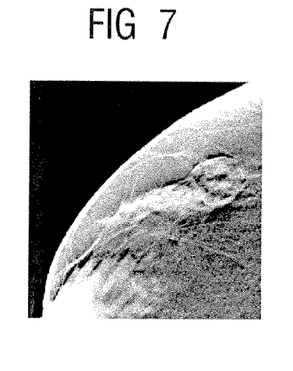
FIGS. 7 through 9 respectively show sections through the breast that are reconstructed with different reconstruction methods.
Figure 8:
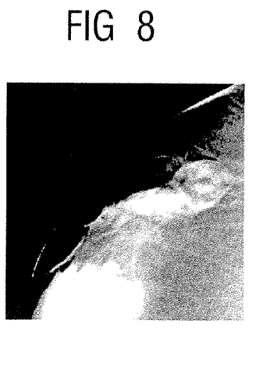
Figure 9:
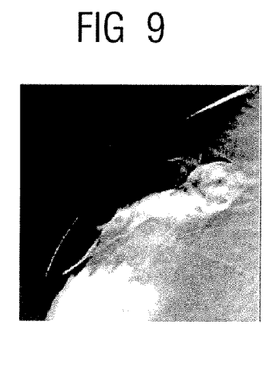

FIGS. 7 through 8 show a section through a breast volume. FIG. 7 was determined by means of a filtered back-projection reconstruction that has a high contrast and a high resolution. However, the brightness of the voxels that correspond to the outer adipose tissue does not differ from the voxels that correspond to the denser tissue at the center point of the breast. FIG. 8 is an iterative maximum likelihood gradient reconstruction without prior functions and noise reduction. A somewhat more realistic density depiction of the breast tissue results. FIG. 9 is an iterative maximum a posteriori reconstruction with a Geman prior function.

Figure 10:
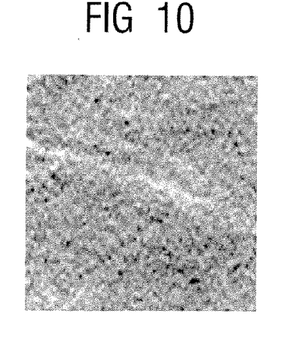
FIGS. 10 through 12 respectively show image reconstructions of the smallest visible vessel that was reconstructed with different reconstruction methods.
Figure 11:
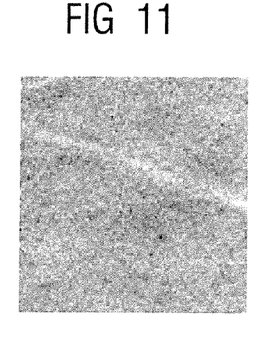
Figure 12:
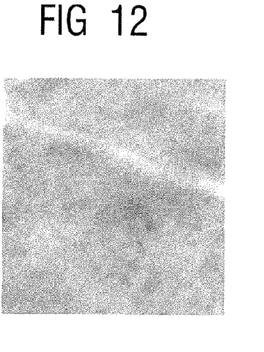

FIGS. 10 through 12 show the thinnest visible vessel in a central section with a feature-free background. FIG. 10 was generated with a filtered back-projection. FIG. 11 was generated by means of five iterations of a maximum likelihood reconstruction without prior functions. FIG. 12 shows a maximum a posteriori reconstruction with a Geman prior function after the fifth iteration.

The invention has the advantage that the noise is reduced and the contrast is increased. Denser tissue—for example glandular tissue—can thereby be differentiated from adipose tissue. Moreover, cancerous tissue can be better differentiated from other tissue, for example adipose tissue, glandular tissue, vessels etc.

Although modifications and changes may be suggested by those skilled in the art, it is the intention of the inventor to embody within the patent warranted hereon all changes and modifications as reasonably and properly come within the scope of his contribution to the art.

I claim as my invention:

1. Method to determine an estimated value of a radiation attenuation coefficient $\mu_j$ of a voxel j that is associated with a segment of a tissue, wherein the attenuation coefficient $\mu$ indicates an attenuation rate of radiation in the tissue, the radiation being emitted with an energy by an emitter and is detected by a detector, the method comprising:

in a computerized processor, automatically obtaining an estimate of the noise value $\Delta\tilde{\mu}$ of the voxel attenuation coefficients $\mu$, from a thickness and density of the tissue and information about the emitted radiation;

in said processor, automatically estimating an average attenuation coefficient $\bar{\mu}$, based on a tissue density estimation and the energy of the radiation emitted by the emitter;

in said processor, automatically calculating parameters of a prior function $U(\mu)$ from the estimated noise value $\Delta\tilde{\mu}$ and the average attenuation coefficient $\bar{\mu}$; and in said processor, iteratively calculating the estimated value of the radiation attenuation coefficient $\mu_j$ of a voxel from projection data acquired by the detector, from the estimated noise value from $\Delta\tilde{\mu}$, the average attenuation coefficient $\bar{\mu}$ and from the prior function $U(\mu)$, and making said estimated value of the radiation attenuation coefficient $\mu_j$ of a voxel available in electronic form at an output of the processor.

2. A method as claimed in claim 1 comprising calculating the parameters of the prior function by calculating parameters of a Geman prior function $U(\mu)$ that has the following equation:

$$U(\mu) = \sum_j \sum_k \frac{\Delta\mu_{jk}^2 \sigma^m}{2\left(\sqrt{\Delta\mu_{jk}^2/2 + \sigma^2/2}\right)^m};$$

wherein $\sigma$ is an optimization parameter and m is a constant, and wherein $\mu_k$ and $\mu_j$ are attenuation coefficients of adjacent voxels that are associated with a respective tissue segment, and j and k are linear voxel indices for three Cartesian dimensions.

3. A method as claimed in claim 2 comprising giving the prior function a convex shape by selecting a so that the first derivative of the prior function has a highest curvature at values of $\Delta\mu$ that correspond to the estimated noise value $\Delta\tilde{\mu}$.

4. A method as claimed in claim 2 comprising giving the prior function a non-convex shape and selecting a so that the first derivative of the prior function has a maximum at values of $\Delta\mu$ that correspond to the estimated noise value $\Delta\tilde{\mu}$.

5. A method as claimed in claim 1 comprising iteratively calculating the expected value of the attenuation coefficient $\mu_j$ of a voxel j using:

$$\mu_j^{n+1} = \mu_j^n + \mu_j^n \frac{\sum_i l_{ij}[d_i e^{-\langle l_i, \mu\rangle} - Y_i] - \beta\frac{\partial}{\partial \mu_j}U(\mu^n)}{\sum_i Y_i l_{ij} + \beta\mu_j^n \frac{\partial^2}{\partial\mu_j^2}U(\mu^n)};$$

wherein $\beta$ is an optimization parameter, $$\langle l_i, \mu\rangle = \sum_j l_{ij}\mu_j, \overline{\sum_i Y_i l_{ij}}$$

is the average value across all voxels of the volume element over all i and j, $Y_i$ is the measured photon count in the projection i and $l_{ij}$ is the section length of a beam of the radiation through the voxel j in the projection i, and determining $\beta$ as:

$$\beta = \frac{\Delta\tilde{\mu} \cdot \overline{\sum_i Y_i l_{ij}}}{\bar{\mu} \cdot \frac{\partial}{\partial\mu_j}U(\mu)\bigg|_{\Delta\mu_j = \Delta\tilde{\mu}} - \Delta\tilde{\mu}\cdot\bar{\mu}\cdot\frac{\partial^2}{\partial\mu_j^2}U(\mu)\bigg|_{\Delta\mu_j=\Delta\tilde{\mu}}}.$$

6. A method as claimed in claim 1 comprising iteratively calculating the estimated value of the attenuation coefficient $\mu_j$ of a voxel j is implemented by:

$$\mu_j^{n+1} = \mu_j^n + \mu_j^n \frac{\sum_i l_{ij}[d_i e^{-\langle l_i,\mu\rangle} - Y_i] - \beta\frac{\partial}{\partial\mu_j}U(\mu^n)}{\sum_i l_{ij}\langle l_i, \mu^n\rangle d_i e^{-\langle l_i,\mu^n\rangle} + \beta\mu_j^n\frac{\partial^2}{\partial\mu_j^2}U(\mu^n)};$$

wherein $\beta$ is an optimization parameter, $$\langle l_i, \mu\rangle = \sum_j l_{ij}\mu_j, \overline{\sum_i Y_i l_{ij}}$$

is the average value across all voxels of the volume element over all i and j, $Y_i$ is the measured photon count in the projection i and $l_{ij}$ is the section length of the beam through the voxel j in the projection i, and calculating $\beta$ as:

$$\beta = \frac{\Delta\tilde{\mu}\cdot\sum_i l_{ij}\langle l_i,\bar{\mu}\rangle d_i e^{-\langle l_i,\bar{\mu}\rangle}}{\bar{\mu}\cdot\frac{\partial}{\partial\mu_j}U(\mu)\bigg|_{\Delta\mu_j=\Delta\tilde{\mu}} - \Delta\tilde{\mu}\cdot\bar{\mu}\cdot\frac{\partial^2}{\partial\mu_j^2}U(\mu)\bigg|_{\Delta\mu_j=\Delta\tilde{\mu}}};$$

wherein $\langle l_i, \bar{\mu}\rangle = \sum_j l_{ij}\bar{\mu}.$

7. A tissue density determination device comprising:

an emitter that emits radiation into tissue having a thickness;

a detector that detects the radiation passing through the tissue;

a computerized noise value estimation device configured to estimate a noise value $\Delta\tilde{\mu}$ of voxel attenuation coefficients $\mu$ from the tissue thickness and information about the emitted radiation;

a computerized tissue attenuation average value estimation device configured to estimate an average attenuation coefficient $\bar{\mu}$, based on a tissue density estimation and the energy of the radiation emitted by the emitter;

a computerized prior function determination device configured to calculate parameters of a prior function $U(\mu)$ from the estimated noise value $\Delta\tilde{\mu}$ and the average attenuation coefficient $\bar{\mu}$; and a computerized iteration device configured to calculate an estimated value of an attenuation coefficient $\mu_j$ of a voxel j from projection data detected by the detector, from the estimated noise value $\Delta\tilde{\mu}$, from the average and estimated tissue attenuation value $\bar{\mu}$ and from the prior function $U(\mu)$, and to make said estimated value of the radiation attenuation coefficient $\mu_j$ of a voxel available in electronic form at an output of the iteration device.

8. A tissue density determination device according to claim 7, wherein the prior function determination device is configured to calculate a Geman prior function $U(\mu)$ that has the following equation:

$$U(\mu) = \sum_j \sum_k \frac{\Delta\mu_{jk}^2 \sigma^m}{2\left(\sqrt{\Delta\mu_{jk}^2/2 + \sigma^2/2}\right)^m};$$

wherein $\sigma$ is an optimization parameter and m is a constant, and wherein $\mu_k$ and $\mu_j$ are attenuation coefficients of adjacent voxels (30) that are associated with a respective tissue segment, and j and k are linear voxel indices over three Cartesian dimensions.

9. A tissue density determination device according to claim 8, wherein the prior function determination device is configured to give the prior function a convex shape by selecting $\sigma$ so that the first derivative of the prior function has a strongest curvature at values of $\Delta\mu$ that correspond to the estimated noise value $\Delta\tilde{\mu}$.

10. A tissue density determination device as claimed in claim 8, wherein the prior function determination device is configured to select a so that the first derivative of the Geman prior function has a maximum at values of $\Delta\mu$ that correspond to the estimated noise value $\Delta\tilde{\mu}$ for non-convex prior functions.

11. A tissue density determination device according to claim 7, wherein the iteration device is configured to determine the estimated value of the voxel attenuation coefficients $\mu_j$ by:

$$\mu_j^{n+1} = \mu_j^n + \mu_j^n \frac{\sum_i l_{ij}[d_i e^{-\langle l_i,\mu\rangle} - Y_i] - \beta \frac{\partial}{\partial \mu_j} U(\mu^n)}{\sum_i Y_i l_{ij} + \beta\mu_j^n \frac{\partial^2}{\partial \mu_j^2} U(\mu^n)};$$

wherein $\beta$ is an optimization parameter, $$\langle l_i, \mu\rangle = \sum_j l_{ij}\mu_j,$$

$Y_i$ is the measured photon count in the projection i and $l_{ij}$ is the section length of a beam of the radiation through the voxel j in the projection i, and wherein the iteration device is configured to determine $\beta$ as:

$$\beta = \frac{\Delta\tilde{\mu} \cdot \sum_i Y_i l_{ij}}{\bar{\mu} \cdot \frac{\partial}{\partial \mu_j} U(\mu)\bigg|_{\Delta\mu_j=\Delta\tilde{\mu}} - \Delta\tilde{\mu} \cdot \bar{\mu} \cdot \frac{\partial^2}{\partial \mu_j^2} U(\mu)\bigg|_{\Delta\mu_j=\Delta\tilde{\mu}}};$$

wherein $\overline{\sum_i Y_i l_{ij}}$ is the average value across all voxels of the volume element over all i and j.

12. A tissue density determination device according to claim 7, wherein the iteration device is configured to determine the estimated values of the voxel attenuation coefficients $\mu_j$ by:

$$\mu_j^{n+1} = \mu_j^n + \mu_j^n \frac{\sum_i l_{ij}[d_i e^{-\langle l_i,\mu\rangle} - Y_i] - \beta \frac{\partial}{\partial \mu_j} U(\mu^n)}{\sum_i l_{ij}\langle l_i, \mu^n\rangle d_i e^{-\langle l_i,\mu^n\rangle} + \beta\mu_j^n \frac{\partial^2}{\partial \mu_j^2} U(\mu^n)};$$

wherein $\beta$ is an optimization parameter, $$\langle l_i, \mu\rangle = \sum_j l_{ij}\mu_j,$$

$Y_i$ is the measured photon count in the projection i, and $l_{ij}$ is the section length of the beam through the voxels j in the projection i, and wherein the iteration device is configured to determine $\beta$ as:

$$\beta = \frac{\Delta\tilde{\mu} \cdot \sum_i l_{ij}\langle l_i, \bar{\mu}\rangle d_i e^{-\langle l_i,\bar{\mu}\rangle}}{\bar{\mu} \cdot \frac{\partial}{\partial \mu_j} U(\mu)\bigg|_{\Delta\mu_j=\Delta\tilde{\mu}} - \Delta\tilde{\mu} \cdot \bar{\mu} \cdot \frac{\partial^2}{\partial \mu_j^2} U(\mu)\bigg|_{\Delta\mu_j=\Delta\tilde{\mu}}};$$

wherein $\langle l_i, \bar{\mu}\rangle = \sum_j l_{ij}\bar{\mu}.$

13. A non-transitory computer-readable storage medium encoded with programming instructions, said storage medium being loaded into a computerized processing system of a tomography apparatus that includes an emitter that emits radiation at an energy, said radiation propagating through tissue and being detected by a detector, said programming instructions operating said processing system to determine an estimated value of a radiation attenuation coefficient $\mu_j$ of a voxel that is associated with a segment of the tissue, said attenuation coefficient $\mu$ indicating an attenuation rate of said radiation in the tissue, and said programming instructions causing said processing system to:
automatically estimate the estimated noise value $\Delta\tilde{\mu}$ of the voxel attenuation coefficients $\mu$, from a thickness of the tissue and information about the emitted radiation;
automatically estimate an average attenuation coefficient $\bar{\mu}$, based on a tissue density estimation and the energy of the radiation emitted by the emitter;
automatically calculate parameters of a prior function $U(\mu)$ from the estimated noise value $\Delta\tilde{\mu}$ and the average attenuation coefficient $\bar{\mu}$; and
iteratively calculate the estimated value of radiation attenuation coefficients $\mu_j$ from projection data acquired by the detector, from the estimated noise value $\Delta\tilde{\mu}$, from the average attenuation coefficient $\bar{\mu}$ and from the prior function $U(\mu)$, and making said estimated value of the radiation attenuation coefficient $\mu_j$ of a voxel available in electronic form at an output of the processing system.

14. A medical system comprising:
an emitter that emits radiation into tissue having a thickness;
a detector that detects the radiation passing through the tissue;

a computerized noise value estimation device configured to estimate noise value $\Delta\bar{\mu}$ of voxel attenuation coefficients $\mu$ from the tissue thickness and information about the emitted radiation;

a computerized tissue attenuation average value estimation device configured to estimate an average attenuation coefficient $\bar{\mu}$, based on a tissue density estimation and the energy of the radiation emitted by the emitter;

a computerized prior function determination device configured to calculate parameters of a prior function $U(\mu)$ from the estimated noise value $\Delta\bar{\mu}$ and the average attenuation coefficient $\bar{\mu}$;

a computerized iteration device configured to calculate an estimated value of an attenuation coefficient $\mu_j$ of a voxel j from projection data detected by the detector, from the estimated noise value $\Delta\bar{\mu}$, from the average estimated tissue attenuation value $\bar{\mu}$ and from the prior function $U(\mu)$, and to make said estimated value of the radiation attenuation coefficients $\mu_j$ available in electronic form at an output of the iteration device; and a display device connected to said output of said iteration device at which said display device visually presents said tissue attenuation coefficients $\mu_j$.

* * * * *